United States Patent [19]

Howarth et al.

[11] 4,102,933

[45] Jul. 25, 1978

[54] PROCESS FOR PREPARING A S-TRIALKOXY BENZENE

[75] Inventors: Barrie D. Howarth, Hexthorte Doncester, England; Ryszard J. Kobylecki, Princeton, N.J.

[73] Assignee: Oce-Andeno B.V., Venlo, Netherlands

[21] Appl. No.: 708,025

[22] Filed: Jul. 23, 1976

Related U.S. Application Data

[63] Continuation of Ser. No. 527,525, Nov. 27, 1974, abandoned.

[51] Int. Cl.² ............................................. C07C 41/04
[52] U.S. Cl. .................................................. 260/613 D
[58] Field of Search ..................................... 260/613 D

[56] References Cited

U.S. PATENT DOCUMENTS

| | | | |
|---|---|---|---|
| 2,803,664 | 8/1957 | Redman | 260/612 D |
| 2,949,488 | 8/1960 | Rocklin | 260/612 D X |
| 3,032,594 | 5/1962 | Towle | 260/612 R |

FOREIGN PATENT DOCUMENTS 1,327,189  4/1963  France.

OTHER PUBLICATIONS

Rubin et al., JACS, vol. 75 (1953), 2517–2519.
Johnson et al., C.A., vol. 34 (1940), 3679.
Benington et al., C.A., vol. 49 (1955), 3208.
McKillop et al., Synthetic Communications, vol. 4 (1974), pp. 35–43.

*Primary Examiner*—Bernard Helfin
*Attorney, Agent, or Firm*—Albert C. Johnston

[57] ABSTRACT

A 1,3,5-trialkoxy benzene having 1–2 carbon atoms in each of the alkoxy-groups is prepared at high overall yields, with minimal formation of hazardous or polluting by-products, by reacting 1,3,5-tribromo benzene with an alkalimetal alcoholate having 1–3 carbon atoms in the molecule in the presence of a copper salt, e.g. cuprous iodide or cupric chloride, and an aprotic solvent such as e.g. dimethylformamide. The product is readily recovered from the reaction mixture in an overall yield as high as 90%.

15 Claims, No Drawings

PROCESS FOR PREPARING A S-TRIALKOXY BENZENE

This is a continuation of application Ser. No. 527,525, filed Nov. 27, 1974 and now abandoned.

This invention relates to a process for preparing a 1,3,5-trialkoxy benzene (s-trialkoxy benzene). More particularly this invention relates to a process for preparing a s-trialkoxy benzene of which each of the alkoxy groups comprises 1 to 3 carbon atoms. The invention also relates to s-trialkoxy benzenes prepared according to the process of the invention.

s-Trialkoxy benzenes havig $C_{1-3}$ alkoxy groups are well known and versatile compounds. They are used e.g. as starting material in the production of other organic compounds. Some of them find application in the textile and pharmaceutical industry.

Hitherto s-trialkoxy benzenes have been prepared mainly by alkylation processes which involve at least two reaction steps. An example of such a process is the acid catalysed alkylation of phloroglucinol with an alcohol, yielding mainly a dialkoxy phenol, followed by alkylation of the last hydroxyl group, e.g. with a dialkylsulphate, in alkaline medium.

The known processes suffer from several disadvantages such as moderate overall yields, the many reaction steps involved and the rigorous reaction conditions required. Another drawback is that not all the required starting materials are readily and/or economically available.

The object of the present invention is to provide a process for preparing a s-trialkoxy benzene in one single reaction step and at high overall yields from a starting material that is readily available.

Accordingly the present invention provides a process for preparing a s-trialkoxy benzene having 1-3 carbon atoms in each of the alkoxy groups, which comprises reacting a s-trihalo benzene with an alkali metal alcoholate having 1 to 3 carbon atoms in the molecule in the presence of a copper salt and an aprotic solvent. Preferably 1,3,5-tribromo benzene is used as the starting material of the process of the invention. When compared with other s-trihalo benzenes it has appeared to be less prone to reduction, which may be a competitive side reaction. Moreover 1,3,5-tribromo benzene is the most readily available of the trihalo benzenes.

The alkali metal alcoholate to be used in the process of the invention can either be added as such to the reaction mixture or it can be formed in situ, e.g. by adding freshly cut sodium or potassium to the alcohol. The use of an excess of alkali metal alcoholate in respect of the s-trihalo benzene was found to be beneficial.

Examples of suitable aprotic solvents are heterocyclic bases such as pyridine, 2-substituted pyridines, γ-picoline and collidine. Preferably, however, tertiary amides such as e.g. N-formyl-morpholine, dimethylacetamide and in particular dimethylformamide are used in the process of the invention. It was found that they act as a kind of co-catalyst, in this way substantially reducing the reaction time required. By applying dimethylformamide e.g. the required reaction time was reduced by some 80% as compared with the reaction times generally required with the pyridine type compounds. Copper (I) salts which can be used in the process of the invention are e.g. cuprous cyanide and cuprous thiocyanide. Very good results were obtained with a cuprous halogenide, especially cuprous iodide. Copper (II) salts, in particular cupric chloride and cupric bromide, were found to be even more effective in that they further reduced the required reaction time at the same level of concentration.

Although the copper salts used in the process of the invention act as a catalyst, more than a trace was found to be necessary for effective catalysis. In general up to 0.3 mole of the copper catalyst per mole of s-trihalo benzene is recommended. However, in the case of tribromo benzene being used as the starting material, and a copper halogenide such as cuprous iodide, cupric chloride or cupric bromide as the catalyst, not more than 0.05-0.15 mole copper-catalyst per mole of s-tribromo benzene was found to be required for obtaining quantitative yields of the s-trialkoxy benzene.

The reaction is carried out at elevated temperatures. Depending on the compositions of the mixture the required temperatures will range from some 80° to 200° C. Advantageously the mixture is heated under reflux. After completion of the reaction, which in most cases is achieved in 10 to 15 hours, the s-trialkoxy benzene can be separated from the reaction mixture and purified by any method known per se, e.g. by low temperature crystallization. Preferably the s-trialkoxy benzene is separated directly from the reaction mixture by distillation. In this way the compound can be obtained in a very pure form in yields well in excess of 90%. The following non-limitative examples will serve to illustrate the invention.

EXAMPLE I

PREPARATION OF 1,3,5-TRIMETHOXY BENZENE

Sodium (4.6 g, 0.2 mole) was dissolved in methanol (40 ml) and to the resulting solution dimethylformamide (40 ml) was added. Cuprous iodide (1.0 g, 0.0026 mole) and 1,3,5-tribromo benzene (10 g, 0.03 mole) were added and the whole mixture was heated under reflux for 2 hours. The hot mixture was filtered to remove inorganic products, cooled, and diluted with water (100 ml), whereupon the bulk of the product precipitated from solution. This was collected by filtration and the remainder of the product was obtained from the aqueous layer by extraction with ether (4 × 30 ml). The combined ether extracts were washed with water, dried ($Na_2SO_4$) and evaporated to give a pale yellow oil. The combined product was then recrystallized from petroleum ether (bp 40°-60°) at −78° C to give 4.1 g (75%) of 1,3,5-trimethoxy benzene as colorless crystals, mp 51-2° C. Direct distillation of the crude reaction mixture prepared in the same way yielded 5.2 g of 1,3,5-trimethoxy benzene (95%). The solubility of the product in petroleum ether was responsible for the lower yields obtained in the first case.

1,3,5-Trimethoxy benzene is known as a useful compound in the pharmaceutical industry. It can also serve as starting material for the preparation of phloroglucinol.

EXAMPLE II

PREPARATION OF 1,3,5-TRIETHOXY BENZENE

To a mixture of 81.6 g sodium ethanolate (1.2 mole) and 400 ml dimethylformamide were added 4 g cupric chloride and 63 g s-tribromo benzene (0.2 mole). The resulting mixture was heated on a water bath during five hours while continuously stirring. When the reaction was completed the excess dimethylformamide was distilled off in vacuum. The residue was treated with water and extracted three times with toluene. The extracts were combined and distilled. In this way 17.6 g of 1,3,5-triethoxy benzene were obtained, having a boiling point of 175° C (24 mm Hg) and a melting point of 42°–43° C.

Having now particularly described and ascertained the nature of our said invention and in what manner the same is to be performed, we declare that what we claim is:

1. A process for preparing a s-trialkoxy benzene having one or two carbon atoms in each of the alkoxy groups, which comprises reacting 1, 3, 5-tribromo benzene with an alkali metal alcoholate having one or two carbon atoms in the molecule in the presence of a copper salt catalyst and an aprotic solvent and recovering formed s-trialkoxy benzene, said catalyst being a cuprous or cupric halogenide and said solvent being a tertiary amide.

2. A process according to claim 1 wherein the alkali metal alcoholate is a sodium or potassium alcoholate.

3. A process according to claim 1 wherein the catalyst is selected from the group consisting of cuprous iodide, cupric chloride and cupric bromide.

4. A process according to claim 1 wherein about 0.05–0.30 mole of said copper salt catalyst is present per mole of 1,3,5-tribromo benzene.

5. A process according to claim 1 wherein the s-trialkoxy benzene is separated from the reaction mixture by direct distillation.

6. A process according to claim 1, said solvent being dimethylformamide.

7. A process for preparing a s-trialkoxy benzene having one or two carbon atoms in each of the alkoxy groups, which comprises reacting s-tribromobenzene with an excess of a sodium or potassium alcoholate having one or two carbon atoms in the molecule in an aprotic solvent comprising a tertiary amide, at a temperature between 80° and 200° C. and in the presence of 0.05 to 0.3 mole of cuprous or cupric halogenide per mole of said benzene, and distilling formed s-trialkoxy benzene from the reaction mixture.

8. A process according to claim 7, said solvent being dimethylformamide.

9. A process according to claim 7, said solvent being dimethylformamide and said alcoholate being sodium methanolate, whereby the product obtained is 1,3,5-trimethoxy benzene.

10. A process for preparing s-trimethoxy benzene which comprises reacting s-tribromo benzene with an excess of sodium methanolate in dimethylformamide and in the presence of 0.05 to 0.15 mole of cuprous iodide per mole of s-tribromo benzene by heating the mixture under reflux, and recovering from the reaction mixture the s-trimethoxy benezene so formed.

11. A process according to claim 10, the amount of sodium methanolate in the reaction mixture being approximately 6 moles per mole of s-tribromo benzene.

12. A process according to claim 10, said recovering being effected by distillation of the reaction mixture.

13. A process for preparing s-triethoxy benzene which comprises reacting s-tribromo benzene with an excess of sodium ethanolate in dimethylformamide and in the presence of about 0.05 to 0.15 mole of cupric chloride per mole of s-tribromo benzene by heating the mixture at approximately water bath temperature, and recovering from the reaction mixture the s-triethoxy benzene so formed.

14. A process according to claim 13, the amount of sodium ethanolate in the reaction mixture being approximately 6 moles per mole of s-tribromo benzene.

15. A process according to claim 13, said recovering being effected by distillation of the reaction mixture or by extraction of the s-triethoxy benzene and distillation of the extract.

* * * * *

UNITED STATES PATENT OFFICE
CERTIFICATE OF CORRECTION

Patent No. 4,102,933  Dated July 25, 1978

Inventor(s) Barrie D. Howarth, and Ryszard J. Kobylecki

It is certified that error appears in the above-identified patent and that said Letters Patent are hereby corrected as shown below:

In the heading on the title page insert:

[30] Foreign Application Priority Data
Dec. 11, 1973  United Kingdom........57428/73

Signed and Sealed this

Thirteenth Day of February 1979

[SEAL]

Attest:

RUTH C. MASON
Attesting Officer

DONALD W. BANNER
Commissioner of Patents and Trademarks

REEXAMINATION CERTIFICATE (900th)

United States Patent [19]

Howarth et al.

[11] B1 4,102,933

[45] Certificate Issued  Jul. 26, 1988

[54] PROCESS FOR PREPARING A S-TRIALKOXY BENZENE

[75] Inventors: Barrie D. Howarth, Hexthorte Doncester, England; Ryszard J. Kobylecki, Princeton, N.J.

[73] Assignee: Oce-Andeno B.V., Venlo, Netherlands

Reexamination Request:
No. 90/001,108, Oct. 6, 1986

Reexamination Certificate for:
Patent No.: 4,102,933
Issued: Jul. 25, 1978
Appl. No.: 708,025
Filed: Jul. 23, 1976

Certificate of Correction issued Nov. 30, 1978.

Related U.S. Application Data

[63] Continuation of Ser. No. 527,525, Nov. 27, 1974, abandoned.

[51] Int. Cl.$^4$ .................... C07C 41/06; C07C 41/01; C07C 43/164
[52] U.S. Cl. .................................................. 568/648
[58] Field of Search ...................................... 568/648

[56] References Cited

PUBLICATIONS

Bacon, et al. "Metal Ions and Complexes in Organic Reactions," Part VIII, J. Chem. Soc. (C) (1969) pp. 308–312.

Bacon, et al. "Metal Ions and Complexes in Organic Reactions, Part XV," J.C.S. Perkin I (1972) pp. 272–278.

Bacon, et al. "Metal Ions and Complexes in Organic Reactions, Part XVI," J.C.S. Perkin I (1972) pp. 278–280.

Bacon, et al. "Metal Ions and Complexes in Organic Reactions, Part IX," J. Chem. Soc. (C) (1969) pp. 312–315.

Bacon, et al. "Metal Ions and Complexes in Organic Reactions, Part X," J. Chem. Soc. (C) (1969) pp. 1978–1981.

*Primary Examiner*—Joseph E. Evans

[57] ABSTRACT

A 1,3,5-trialkoxy benzene having 1-2 carbon atoms in each of the alkoxy-groups is prepared at high overall yields, with minimal formation of hazardous or polluting by-products, by reacting 1,3,5-tribromo benzene with an alkalimetal alcoholate having 1–3 carbon atoms in the molecule in the presence of a copper salt, e.g. cuprous iodide or cupric chloride, and an aprotic solvent such as e.g. dimethylformamide. The product is readily recovered from the reaction mixture in an overall yield as high as 90%.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-15 are cancelled.

* * * * *